United States Patent [19]

Law

[11] Patent Number: 4,902,466
[45] Date of Patent: Feb. 20, 1990

[54] PROCESS FOR MAKING LIPID FILMS SUITABLE FOR LIPOSOMES

[75] Inventor: Say-Jong Law, Westwood, Mass.

[73] Assignee: Ciba Corning Diagnostics Corp., Medfield, Mass.

[21] Appl. No.: 940,571

[22] Filed: Dec. 11, 1986

[51] Int. Cl.$^4$ ............................................. G01N 33/92
[52] U.S. Cl. ................................... 264/299; 264/101; 264/202; 264/212; 264/217; 436/71; 436/829
[58] Field of Search ............... 264/204, 202, 212, 299, 264/101, 217; 436/71, 829

[56] References Cited

U.S. PATENT DOCUMENTS

| | | | |
|---|---|---|---|
| 3,152,203 | 10/1964 | Dumitau | 264/212 |
| 4,342,826 | 8/1982 | Cole | 436/829 |
| 4,485,054 | 11/1984 | Mezei et al. | 436/829 |
| 4,588,578 | 5/1986 | Fountain et al. | 436/829 |
| 4,608,211 | 8/1986 | Handjani et al. | 436/829 |

Primary Examiner—Hubert C. Lorin
Attorney, Agent, or Firm—William G. Gosz

[57] ABSTRACT

A method for forming lipid films having a substantially uniform thickness and a ratio of the surface area of deposited film to lipid concentration of less than 600 cm$^2$ per mmole. Using a substantially flat stationary surface for lipid depositation and evaporation results in the formation of lipid films suitable for commercial production of liposomes.

3 Claims, 1 Drawing Sheet

PROCESS FOR MAKING LIPID FILMS SUITABLE FOR LIPOSOMES

The present invention relates to a method for forming lipid films having a substantially uniform thickness and ratio of the surface area of deposited film to lipid concentration of less than 600 cm$^2$ per millimole. Using a substantially flat stationary surface for lipid depositation and evaporation results in the formation of lipid films suitable for commercial production of liposomes.

BACKGROUND ART

The formation of liposomes from the hydration of lipid films is well known in the art. However, a major barrier to large scale, economic production of liposomes was the fact that the precursor lipid films had to be very thin. As a result, from a manufacturing perspective, excessive amounts of surface area were required to yield a given amount of liposomes.

The primary method of forming lipid films was by means of conventional rotary evaporation of lipid solutions in round bottom flasks. Films produced by this means were not of a uniform thickness or surface area and required at least 600 cm$^2$ of surface area for each mmole of lipid solution. Thus, the production of liposomes from a typical desired lot, i.e., 12 mmoles of lipid, required a 50 liter flask. Moreover, liposomes formed by hydrating the uneven film, were found to have an unacceptable degree of variability. For example, when liposomes made by prior methods were used in the liposome immunoassay disclosed in U.S. Pat. No. 4,342,826, issued to Francis X. Cole, the performance of the assay was unacceptable in terms of the reproducibility of signal output and standard curves on a batch to batch basis.

DISCLOSURE OF THE INVENTION

The present process enables the artisan to produce lipid films of a substantially uniform thickness which, in turn, are needed to produce liposomes of commercial value for use in immunoassays. Moreover, it allows for large batch production without concomitantly requiring very large surface areas for depositing the lipid. For example, less than 140 cm$^2$ of surface area can accommodate one mmole of lipid.

Unlike the prior art, in the two steps of the present process one must maintain the depositation/evaporation surface in a stationary, horizontal position. Moreover, this surface must be substantially flat, i.e. level. If one deposits a lipid solution on such a surface, then evaporates the lipid either by vacuum or ambient pressure, then the resultant lipid film can be easily hydrated to form liposomes suitable for use in immunoassays.

MODES OF THE INVENTION

By using a substantially level surface in a stationary horizontal position for the depositing and, evaporating of the lipid solution one can produce a thicker lipid film of a uniform thickness that is highly suitable for the preparation of liposomes used in immunoassays. A preferable depositation/evaporation surface for the present method is simply a circular, level (i.e., within 1 mm.) piece of plate glass fused to an annular piece of glass having a height such that combined, a well is formed with a vertical wall sufficient to contain the amount of lipid solution which is poured into the well.

Figure 1:
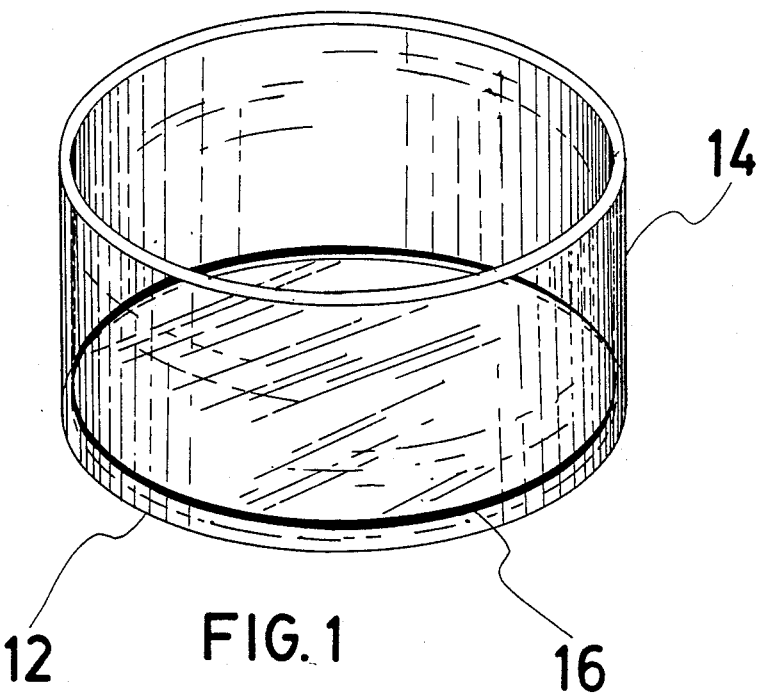
FIG. 1 is a perspective of a preferred means for performing the present method.
Figure 2:
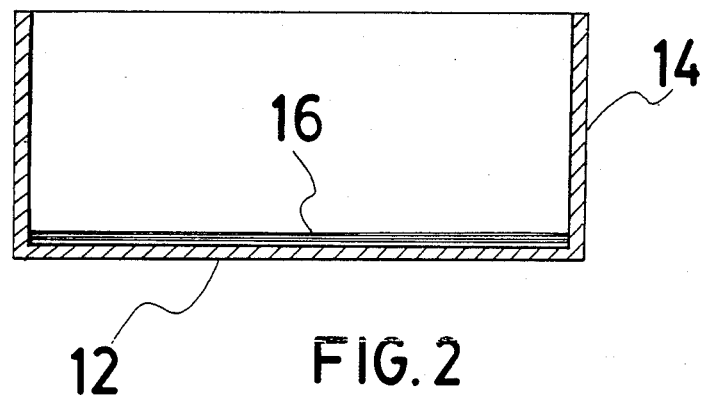
FIG. 2 is a cross-sectional view of vessel on which the lipid film is formed.

As an example of the present process, a lipid solution was made by combining 3000 mg of a lipid mixture comprised of 1875 mg of dipalmitoyl phosphatidylcholine (DPPC), 1010 mg of cholesterol, and 115 mg. of dipalmityl phosphatidylglycerol (DPPG), with 80 ml of chloroform. Referring to FIGS. 1 and 2, the solution was poured into a circular glass vessel (12) having a depositing surface (16) with a 30 cm diameter, and a retaining wall (14) that is 100 mm high. The depositing surface was within 1 mm. of level over the entire surface. The chloroform was evaporated from the solution by a two-stage method at room temperature. An air-permeable lid was affixed over the dish and a low vacuum of 20–100 Torr was used to evaporate about 95% of the chloroform in a 5 to 8 hour period. The remainder was removed by increasing the vacuum to below 10 milli-Torr overnight, resulting in a lipid film having a surface area to lipid concentration ratio of less than 140 cm$^2$/mmole.

It should be apparent to one having ordinary skill in the art that many variations are possible without departing from the spirit and scope of the invention.

I claim:

1. A process for forming lipid films of a substantially uniform thickness, having a surface area of deposit to lipid concentration ratio of less than 600 cm$^2$/mmole, comprising depositing a lipid solution in a stationary vessel having a substantially level horizontal surface, then evaporating the liquid so as to form a lipid film while maintaining the vessel in a stationary horizontal position.

2. The process of claim 1 wherein the substantially level horizontal surface is level to within a tolerance of one millimeter over the depositing surface.

3. A process for forming liposomes by hydration of a lipid film comprising adding a liquid to a lipid film made by depositing a lipid solution in a stationary vessel having a substantially level horizontal surface, then evaporating the liquid so as to form a lipid film while maintaining the vessel in a stationary horizontal position.

* * * * *